(12) United States Patent
Bhown (10) Patent No.: US 6,485,650 B1
(45) Date of Patent: Nov. 26, 2002

(54) LIQUID MEMBRANE SEPARATION OF ENANTIOMERS

(75) Inventor: Abhoyjit Singh Bhown, Fremont, CA (US)

(73) Assignee: Facilichem, Inc., Menlo Park, CA (US)

( * ) Notice: Subject to any disclaimer, the term of this patent is extended or adjusted under 35 U.S.C. 154(b) by 0 days.

(21) Appl. No.: 09/649,292

(22) Filed: Aug. 28, 2000

(51) Int. Cl.[7] .......................... B01D 63/02; B01D 61/38
(52) U.S. Cl. .................. 210/643; 210/638; 210/321.87; 95/44
(58) Field of Search ................................. 210/643, 638, 210/321.8, 321.87; 96/5; 95/44

(56) References Cited

U.S. PATENT DOCUMENTS

| | | | |
|---|---|---|---|
| 4,743,189 A | | 5/1988 | Samuelson |
| 4,789,468 A | | 12/1988 | Sirker |
| 4,800,162 A | | 1/1989 | Matson |
| 4,834,881 A | | 5/1989 | Sawada et al. |
| 4,941,812 A | | 7/1990 | Samelson |
| 4,960,762 A | | 10/1990 | Sellergren et al. |
| 5,002,871 A | * | 3/1991 | Iacobucci |
| 5,037,741 A | * | 8/1991 | Iacobucci |
| 5,077,217 A | | 12/1991 | Matson et al. |
| 5,080,795 A | | 1/1992 | Pirkle et al. |
| 5,147,541 A | | 9/1992 | McDermott, Jr. et al. |
| 5,167,824 A | * | 12/1992 | Cohen et al. |
| 5,202,235 A | * | 4/1993 | Iacobucci |
| 5,254,258 A | | 10/1993 | Pirkle et al. |
| 5,256,293 A | * | 10/1993 | Pirkle et al. |
| 5,266,195 A | | 11/1993 | Hopkins |
| 5,275,726 A | | 1/1994 | Feimer et al. |
| 5,290,440 A | | 3/1994 | Pirkle et al. |
| 5,490,926 A | | 2/1996 | Hemmeken |
| 5,578,212 A | | 11/1996 | Pirkle et al. |
| 5,580,452 A | | 12/1996 | Lin |
| 5,770,084 A | | 6/1998 | Warner et al. |
| 6,013,738 A | | 1/2000 | Daly et al. |
| 6,086,769 A | * | 7/2000 | Kilambi et al. |
| 6,096,217 A | * | 9/2000 | Kilamby et al. |

FOREIGN PATENT DOCUMENTS

| | | |
|---|---|---|
| WO | 98 10852 | 3/1998 |
| WO | 98 33581 | 8/1998 |

OTHER PUBLICATIONS

D. K. Mandal et al. "Isomer Separation by a Hollow Fiber Contained Liquid Membrane Permeater", Journal of Membrane Science, Elsevier Scientific Publ. Company, Amsterdam, NL, vol. 144 (1998), pp. 13–24.

Database WPI, Section Ch, Week 200024, Derwent Publications Ltd., London, GB; AN 2000–283785 "XP002191184" & ZA 9906510A (Univ. Potchefstroom) Jan. 26, 2000, Abstract.

"Chiral Separations Applications and Technology", Satinder Ahuja, Editor, American Chemical Society Publication, 1996, Chapter 6, pp. 139–154, Chapter 7, pp. 155–172, and Chapter 11, pp. 309–334.

* cited by examiner

*Primary Examiner*—Ana Fortuna
(74) *Attorney, Agent, or Firm*—Hudak, Shunk & Farine Co.

(57) ABSTRACT

The invention is related to a method for separating enantiomers in a supported liquid membrane module by contacting the liquid membrane which may contain a carrier and a phase transfer agent with a feed fluid containing a racemic mixture whereby an enantiomer is transported into the liquid membrane and thereafter contacting the liquid membrane with a sweep fluid whereby an enantiomer is transported from the liquid membrane into the sweep fluid. The enantiomer is then recovered from the sweep fluid. The liquid membrane module is constructed in such a way that the feed fluid and the sweep fluid are adjacent to, but on opposite sides of, the liquid membrane and the feed and sweep fluids have a substantially continuous interfacial contact along the length of the liquid membrane.

32 Claims, 7 Drawing Sheets

FIG. 1

FIG. 1a
LIQUID MEMBRANE MODULE

FIG. 1b (DATA FROM EXAMPLE 1)

- Produce both enantiomers with high % ee
- Near 100% Yield

- Produces both enantiomers with high % ee
- 99% ee demonstrated in stages

LIQUID MEMBRANE SEPARATION OF ENANTIOMERS

BACKGROUND OF THE INVENTION

This invention relates to the separation of enantiomers or a racemic mixture, into the specific isomers.

Stereoisomers are those molecules which differ from each other only in the way their atoms are oriented in space. Stereoisomers are generally classified as diasteromers or enantiomers; the latter embracing those which are mirror images of each other, the former being those which are not. The particular arrangement of atoms that characterize a particular stereoisomer is known as its optical configuration, and are generally identified as either + or − (also D or L) (and d or l) or R or S.

Though differing only in orientation, the practical effects of stereoisomerism may be important. For example, the biological and pharmaceutical activities of many compounds are strongly influenced by the particular configuration involved. Many compounds are only of widespread utility when provided in a given stereoisomeric form. Therefore, it is the separation of enantiomers that presents a special problem because their physical properties are identical. This is particularly true when involving a racemic mixture; that is, a mixture that comprises equal amounts of enantiomers having different optical configurations. Separation of the racemate into its respective enantiomers, generally known as a resolution, is, therefore, a process of considerable importance and challenge.

A number of techniques for separating enantiomers are known in the art such as various chromatographic methods or enzyme-catalyzed reactions. Most, however, are useful for obtaining small analytical quantities and are not practical for separating larger quantities for commercial purposes. One such method is known as an indirect separation which involves reacting the enantiomers with an optically pure chiral derivatizing agent. A direct method of separation is much like the indirect method involving the formation of a diasteromeric species which is transient, with the stability of one species differing from the other.

Another method described in U.S. Pat. Nos. 4,800,162 and 5,077,217 utilizes multi-phase and extractive enzyme membrane bioreactors for the resolution of racemic mixtures of optically active compounds.

Liquid membranes have been used for separating enantiomers as discussed in the book Chiral Separation, Applications and Technology, S. Ahuja, Editor; American Chemical Society, 1997, Chapter 11, pp. 309–334. One system is described on pp. 329–330, where two membrane modules are employed.

U.S. Pat. No. 5,080,795 to Pirkle et al. employs a similar supported chiral liquid membrane and a chiral carrier which selectively complexes with one of the two enantiomeric optical configurations. However, the liquid membrane present in the Pirkle et al. patent is used in a totally different manner so that in fact the apparatus is in effect a contactor rather than a liquid membrane. The disclosed apparatus has a different principle of operation and different engineering basics compared to the apparatus employed in the present invention. As is clearly shown in the Pirkle et al. patent, the liquid membrane must flow from the source phase containing the feed liquid to the receiving phase containing the solution enriched with one enantiomer. In that respect, the method of separating enantiomers disclosed by Pirkle et al. is totally different from the method of this invention.

Thus, although liquid membranes have been known to be useful in separating chiral enantiomers, they have never been used commercially because, depending on the design and the materials used, the separation modules or parts thereof deteriorate rather quickly or the necessary ingredients such as the liquid membrane or the carrier are partially lost in the process and the separation must be periodically interrupted to replace or replenish them. Furthermore, the prior art methods are often batch processes and, even if continuous, could not be adapted for a large scale continuous separation. Such processes do not provide the necessary rate of transport and the degree of separation in a reasonable time period to make them feasible for large scale commercial enantiomer separation. These deficiencies are resolved and eliminated by the method of this invention.

DETAILED DESCRIPTION

The present invention is directed to a method for separating or resolving enantiomers in a supported liquid membrane module which comprises a liquid membrane, feed fluid containing a racemic mixture and a sweep fluid into which the separated enantiomer passes, such that said feed fluid and said sweep fluid are adjacent to, but on opposite sides of, said liquid membrane and the feed fluid and the sweep fluid have a substantially continuous interfacial contact along the length of the liquid membrane, said method comprising:

a) contacting liquid membrane with said feed fluid;

b) transporting preferentially one enantiomer from the feed fluid into the liquid membrane;

c) contacting liquid membrane with said sweep fluid;

d) transporting the enantiomers from the liquid membrane into the sweep fluid; and e) recovering the enantiomers from the sweep fluid.

The feed fluid may be composed only of the enantiomers or optionally it may also contain a solvent. If the enantiomers are solid, then a solvent must be employed to dissolve the solid enantiomers. If the enantiomers are liquid, a solvent is usually not absolutely necessary but it may be desirable to employ a solvent. If the selectivity of one enantiomer by the liquid membrane is high, then substantially only one isomer will transport through the membrane and the separation of the isomers will be substantially complete. Optionally, the liquid membrane may also contain a phase transfer agent (PTA) which can be any chemical agent to aid the partitioning of an enantiomer from the feed fluid into the liquid membrane. The feed fluid pH could be adjusted to favor the solubility of the enantiomers in the liquid membrane. Likewise, the sweep fluid pH could be adjusted to favor the solubility of the enantiomers in the sweep fluid.

The solvent that may be employed in the feed must dissolve the enantiomers but it must be different than the solvent in the liquid membrane and it must be substantially immiscible with the liquid membrane. Nevertheless, the solvent could be the same as the solvent in the sweep.

Those skilled in the art will be informed what solvents could be used for a particular enantiomer and the literature provides much information in this regard. For example, a discussion is provided in Chiral Separations, S. Ahuja, ed., (1996) p. 283.

A membrane is a semi-permeable barrier that spatially divides two solutions of different concentrations and controls the solute exchange rate between them. A liquid membrane can serve as a membrane between two other liquid phases provided it is immiscible with those liquid phases.

The liquid membrane in the invention consists of a liquid that is immiscible with the feed and the sweep fluids and preferentially dissolves the enantiomer that is to be isolated. The liquid membrane optionally may also contain a carrier and a phase transfer agent (PTA). The need for a carrier and a PTA will depend on the enantiomers that are being separated, the degree of solubility of the desired enantiomer in the liquid membrane (i.e., the solvent present in the liquid membrane), the enantios electivity and the flux rate across the membrane.

A chiral carrier is a material that enhances the rate of selective transport of an enantiomer. Generally, a chiral carrier complexes preferentially with one enantiomer in the liquid membrane or dissolves preferentially one enantiomer. In effect, the carrier increases the solubility of one enantiomer in the liquid membrane. This facilitates the transport of the complexed or the preferentially soluble enantiomer through the liquid membrane. Thus, a solvent used as a liquid membrane could conceivably act as a carrier. The uncomplexed carrier and the carrier complexed with an enantiomer should be substantially immiscible with the feed and sweep fluids. The carrier, if present, must have a degree of solubility in the solvent which constitutes the major portion of a liquid membrane. It is preferable that the carrier have substantial solubility in the solvent and it is further preferable that it be close to its maximum concentration in the liquid membrane. Generally the greater the concentration of the carrier, the greater the flux. For practical reasons, however, there will be an optimum range of the concentration to provide good flux without increasing the cost unreasonably. The topic of flux and related subjects are discussed in Cussler E. L., "Diffusion: Mass Transfer in Fluid Systems," Cambridge University Press (1984 ed.), pp. 395–400.

The literature generally contains much information regarding the carriers for specific enantiomers. For example, the list in the following Table is illustrative of the literature disclosing appropriate carriers for the indicated enantiomers.

TABLE

| ENANTIOMERS | CARRIERS |
|---|---|
| Leu-methyl ester | dibenzo-18-crown-6 (DB18C6) and its acyl derivatives containing aliphatic chains of various lengths |
| Glu | Nopol<br>(2S)-(–)-methyl-l-butanol<br>2,3:4,5-bis[1,2-(3-phenylnaphtho)]-1,6,9,12,15,18-hexaoxacycloeicosa-2-4-diene |
| Amino Acid hydrochlorides | Nopol<br>(2S)-(–)-methyl-l-butanol |
| 3-hydroxytryosine (Dopa) | 2,3:4,5-bis[1,2-(3-phenylnaphtho)]-1,6,9,12,15,18-hexaoxacycloeicosa-2-4-diene |
| Novaline | 2,3:4,5-bis[1,2-(3-phenylnaphtho)]-1,6,9,12,15,18-hexaoxacycloeicosa-24-diene |
| Ephedrine | S.S. or R.R-dihexyltartrate (DHT) |
| Mirtazpine | S.S. or R.R-dihexyltartrate (DHT)<br>Poly(lactic acid)PLA)<br>Dibenzoyltartaric acid (DBT) |
| Phenylglycine | S.S. or R.R-dihexyltartrate (DHT)<br>2,3:4,5-bis[1,2-(3-phenylnaphtho)]-1,6,9,12,15,18-hexaoxacycloeicosa-2-4-diene<br>Chiral crown ether containing a methyl a-D-mannopyranoside unit<br>18-crown-6 ether with a D-mannopyranoside unit and a naphthalenemoiety |
| 1-phenylethylamine | 2,3:4,5-bis[1,2-(3-phenylnaphtho)]-1,6,9,12,15,18-hexaoxacycloeicosa-2-4-diene |
| 1-phenyl-2-aminopropane | 2,3:4,5-bis[1,2-(3-phenylnaphtho)]-1,6,9,12,15,18-hexaoxacycloeicosa-2-4-diene |

As can be seen in the above Table, for some enantiomers there may be only one known carrier, but for others, there may be a choice of several carriers. Those skilled in the art will understand that chromatography can be used as a screening tool to determine which materials can be used as carriers for specific enantiomers. For example, a prospective carrier is placed in the column packing and a feed fluid containing specific enantiomers is injected into the column. If the column separates the enantiomers, then the test material in the column can be used as the carrier in the method of this invention. If the carrier is a solid, then a solvent must be employed to dissolve the carrier. The solvent may be achiral or chiral. But the carrier itself must be chiral because it must have preference for one enantiomer over the other.

As mentioned above, PTA must not necessarily be included in the liquid membrane, but it may be advantageous to have a PTA present. The phase transfer agent (PTA) in general is a non-covalent molecular associate of a specific substrate which drastically alters the solubility profile of the substrate. Examples of this are (a) for an ionic substrate, a large counter ion that will form an ion pair with the ionic substrate, causing the ion pair to be soluble in a media in which the original ion is not soluble; (b) for a non-ionic substrate, a PTA might engage in a weak interaction with the non-ionic substrate or may complex with such substrate with the result that the resulting substrate has a qualitatively different solubility property than the original substrate. In nature, all the protein carriers in a human or animal body act as PTAs.

The amount of a PTA used in a liquid membrane will depend on its ability to complex and to transport an enantiomer. As an example, the concentration of a PTA may range from an extremely minor amount such as 0.1 mmole up to 10 mmoles, or even up to 100 mmoles and in the case of an ionic PTA, it could even approach 1 mole. The discussion of the use of PTA may be found in the publication of Pirkle et al., "Use of Achiral Ion-Pairing Reagents With Chiral Stationary Phases", J. of Chromatography, 479 (1989), pp. 377–386.

If neither a carrier nor a PTA is employed, a separation is possible only if the solvent has selectivity for one enantiomer over the other. However, if both enantiomers are equally soluble in that solvent, then no separation is possible without a carrier. If the solvent is chiral, then generally one enantiomer will be preferentially soluble in such a chiral solvent. For example, if Nopol is used as a liquid membrane, then one enantiomer from a mixture of amino acid enantiomers will be transported substantially faster than the other enantiomer through such a liquid membrane and separation will occur even without a carrier (Bryjak et al., J. Memb. Sci., 85, 221, 1993. If, however, achiral liquid membrane is employed, generally no separation of enantiomers will occur without the use of a carrier or a PTA.

The sweep fluid, sometimes also referred to as the strip or purge fluid, is the fluid into which preferentially one enantiomer passes from the liquid membrane. The sweep fluid is generally a liquid consisting of a solvent and optionally an enantiomer solubility enhancer, a material that would aid the release of the enantiomer from the carrier in the liquid membrane. Such a material can also strongly increase the solubility of the enantiomer in the sweep. Examples of solubility enhancers include acids and bases to alter the pH of the sweep. The solvent in the sweep must be different than the solvent in the liquid membrane but it can be the same as the solvent in the feed fluid. It could be chiral or achiral. The solvent in the sweep must be substantially immiscible with the liquid membrane. The pH of the sweep and also of the feed fluid can be adjusted by using an appropriate buffer to maximize the solubility of one enantiomer or to provide a pH gradient between the feed and the sweep to favor active transport of the enantiomer from the feed to the sweep fluid. For example, in the separation of the racemic mixture of N-(3,5-dinitrobenzoyl) leucine, the sweep is water. Potassium dihydrogen phosphate, $KH_2PO_4$, is used as a buffer to adjust the pH. Generally it is preferable to adjust the pH of the sweep to maximize the solubility of one enantiomer in the sweep.

In the present invention, the liquid membrane may be stationary or it may be moving or flowing from one location to the other. The two locations, however, are anywhere where there is no area for mass transfer between the first location and the second location. That means, it could be flowing anywhere where the liquid membrane is not directly between the feed and the sweep fluids. The flow of the liquid membrane may be in any direction or stationary. Even if one or both of the fluids and the liquid membrane are stationary, the enantiomers can still be transported across from the feed fluid through the liquid membrane, and into the sweep fluid. This transport occurs if the concentration of the enantiomer is higher in the feed fluid relative to the sweep, or there is active transport by coupled facilitated diffusion. The literature defines conditions when these occur, e.g. E. L. Cussler, "Diffusion: Mass Transfer in Fluid Systems," Cambridge University Press (1984 ed.), p. 402. It is generally preferable that the fluids be moving, either in the same direction or in the opposite direction. A diagrammatic illustration of the relative locations of the various fluids and a specific example of the flow of the fluids is shown in FIG. 1a.

It should be understood that the walls of the liquid membrane contain pores. These pores are always filled with one of the fluids present in the module, i.e., the feed fluid, liquid membrane fluid or sweep fluid. It is a preferred feature of this invention to have a particular type of a fluid in the pores depending on the level of partitioning of the enantiomers or enantiomers. For enantiomers that have poor partitioning into the liquid membrane, the pores of the fiber walls of the liquid membrane should preferably be filled with the feed and/or sweep fluids because the enantiomers are more soluble in the feed and the sweep than in the liquid membrane and it is desirable that the concentration of the enantiomer be as high as possible in the walls.

For enantiomers that have high or good partitioning in the liquid membrane, i.e., enantiomers more soluble in the liquid membrane solvent then in the feed or sweep fluids, the walls preferably should be filled with the liquid membrane. When the pores of the fiber is filled with a particular fluid, it may be said that the fiber walls are wetted with that fluid. It is more common that the majority of enantiomers have poor partitioning into the liquid membrane. In such cases, it is preferable that the fiber material for tubular membranes be chosen so that the pores of the fibers are filled with the feed and sweep fluids. Spacers are required to ensure that there is no contact between the inner and the outer fiber, that is, so that there is no direct contact between the feed and the sweep fluids.

Any enantiomers may be separated employing the method of this invention, regardless of the chemical nature of the enantiomers. Thus, optically active organic amines, amides, nitrites, carboxylic acids, esters, alcohols, hydantoins and other optically-active compounds may be separated into the individual enantiomers. The separated enantiomers may be useful in pharmaceuticals, agricultural, chemicals, fragrances, flavoring agents and other applications.

The method of this invention is particularly useful in separating enantiomers on a commercial scale because the separation is efficient and economical. All parts of the module are of a substantially permanent nature and are not used up, requiring frequent interruption in the operation for the purpose of replacing any used-up parts. Furthermore, the separation could be carried out in a continuous process. The actual rate of separation will depend on the specific enantiomers being separated, the solvents used, the carrier and PTA used, the size of the unit, the degree of buffering and the temperature at which separation is conducted.

The separation of enantiomers described above may be accomplished in a tubular or hollow liquid membrane module that is particularly effective on a commercial scale. The liquid membrane can be stationary or moving, although the latter is preferred. The module has a housing which is adapted to contain at least one tubular liquid membrane element. The element includes a first tubular membrane located within a second tubular membrane with an annular gap defined between the first tubular membrane and the second tubular membrane. The first (inner) tubular membrane, which generally may have an inside diameter (I.D.) of about 50 microns to about 2 mm and wall thickness of 10 microns to 500 microns, is longer than the second tubular membrane so that its ends extend axially out of the ends of the second tubular membrane. The outer tubular fiber may generally have I.D. of about 100 microns to about 3 mm with the same wall thickness as the thinner tube. Also, a screen spacer/support may be used in the annular space or gap between the inner and outer tubes to provide mechanical support for the tubular membranes. The liquid membrane is housed or contained in the annular space and as the liquid flows, the spacers/screens create mixing of the liquid membrane. Spacers can be made from any material such that it prevents direct contact between the inner and outer fiber along the length of the fiber. The annular space is generally from about 10 microns to about 500 microns but typically between about 20 and 50 microns. Generally, smaller annular spaces and thinner wall thicknesses of the tubular membrane are preferred because this creates less resistance to diffusion. The membranes are 20% to 80% porous and more typically about 30% to 50%. The pore sizes in the membranes are between about 0.01 microns to about 10 microns but the smaller pores are preferred if a high pressure drop is applied between the feed and sweep fluids. The overall size of the module is application dependent. A module must contain at least one set of membranes (one inner and one outer tubular membrane) but it may contain hundreds or thousands of them. The more membrane sets, the larger the volume of enantiomers that may be separated per unit time. Thus, the module size may be 10–12 inches in diameter and up to about 3 feet long. There is a theoretical limit to the size of the module if good separation of enantiomers is to be maintained.

The lumen of the first tubular membrane is used as fluid passage for the feed fluid, and the outer surface of the second tubular membrane is used as fluid flow surface for the sweep fluid. Alternatively, the lumen of the first or inner tubular membrane can be used as the fluid passage way for the sweep fluid and the outer surface of the second or outer tubular membrane can be used for the passage of the feed fluid.

The module also includes four tube sheets, two at each end of the housing. At one end of the housing, a first tube sheet extends between the housing and the exterior surface of the first end of the first (inner) tubular membrane, and the second tube sheet extends between the housing and the exterior surface of the first end of the second (outer) tubular membrane. The space between the first and second tube sheets is used as a membrane liquid intake manifold for providing a membrane liquid from a membrane liquid inlet port on the housing to the annular gap.

At the other end of the housing, a third tube sheet extends between the housing and the exterior surface of the second end of the first tubular membrane, and fourth tube sheet extends between the housing and exterior surface of the second end of the second tubular membrane. The space between the third and fourth tube sheets is used as a membrane liquid outlet manifold for removing a membrane liquid from the annular gap at a membrane liquid outlet port on the housing.

The space between the first tube sheet and the housing is used as a feed intake manifold for providing a feed fluid from a feed fluid inlet port in the housing to the fluid passage way. Likewise, the space between the third tube sheet and the other end of the housing is used as a feed fluid outlet manifold for removing a feed fluid from the fluid passage way to a feed fluid outlet port in the housing.

A sweep fluid inlet port is formed in the housing between the second tube sheet and a fourth tube sheet. This port facilitates the introduction of a sweep fluid from a sweep fluid to the fluid flow surface. The sweep fluid outlet port is located on the other side of the housing, spaced from the sweep fluid inlet port. The sweep fluid outlet port facilitates the removal of the sweep fluid from the fluid flow surface at a sweep fluid outlet port on the housing. As already mentioned above, the conduits for the feed and sweep fluids may be interchanged. If the enantiomers are gaseous, the module may also be operated when the sweep fluid is in gas phase. In such a module, the sweep fluid inlet port is closed and a vacuum pump and/or a condenser is connected to the sweep fluid outlet port to draw the enantiomer out of the module from the enantiomer-enrichment channels. Alternatively, a sweep fluid may be used to remove the separated enantiomer.

In addition, the Tubular or Hollow Fiber module includes various connections to the element for providing independent and simultaneous flowing of a feed fluid through the fluid passageway, a membrane liquid through the membrane liquid passageway, and a sweep fluid upon the fluid flow surface. These connections include differential pressure controllers, fluid pumps, and a membrane liquid reservoir.

BRIEF DESCRIPTION OF THE DRAWING

Various views of a liquid membrane module employed in the method of the present invention are described below in reference to the following figures wherein like numerals represent like parts.

DETAILED DESCRIPTION OF THE LIQUID MEMBRANE MODULE

Figure 1:
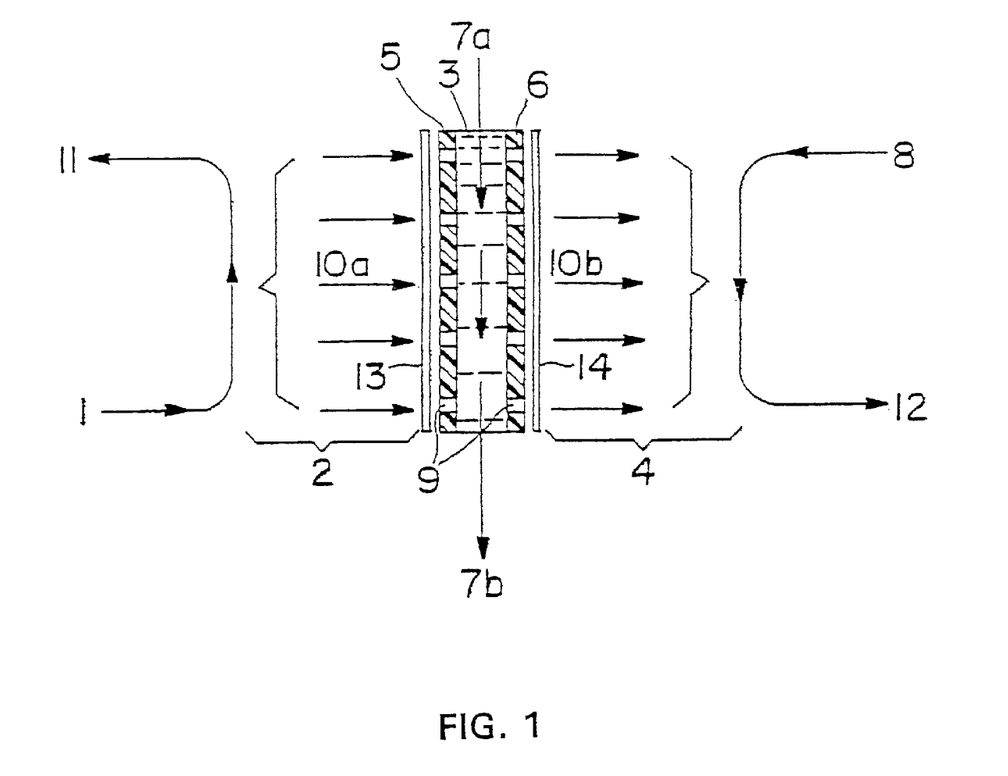
FIG. 1: is a general illustration of the elements of a liquid membrane employed in the present invention.
Figure 1A:
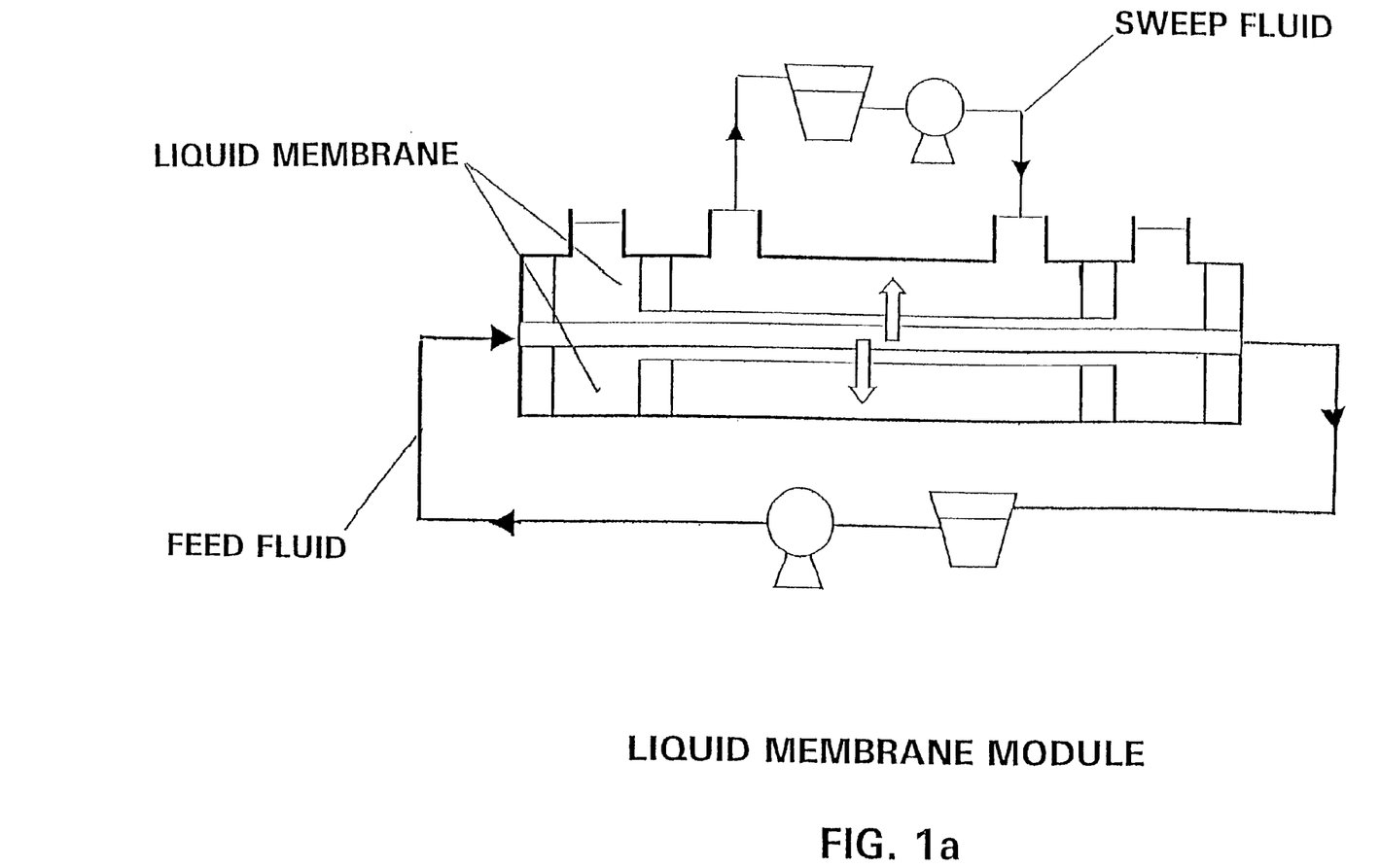
FIG. 1a: is a general illustration of a liquid membrane module showing the relative locations of the various fluids.

The structure of a Liquid Membrane System is generally depicted in FIG. 1. A feed fluid 1 passes through the enantiomer depletion channel 2 defined on one side of the Liquid Membrane channel 3 (LM). On the other side of the LM, an enantiomer-enrichment channel is defined through which a sweep or strip fluid 8 flows. The LM separates the enantiomer-depletion channel from the enantiomer-enrichment channel and prevents direct communication between the feed and sweep fluids. These three channels form a permeation element which permits the selective transport of a enantiomer 10a, 10b from feed fluid to sweep fluid 8 resulting in a enantiomer depleted feed fluid 11 and a enantiomer enriched sweep fluid 12.

The porous walls 5, 6 serve as interface media through which the enantiomers pass from the feed fluid 1, the membrane liquid 7a, 7b, and into sweep fluid 8. These walls may or may not be wetted by the membrane liquid, and the pores 9, in the walls may be filled with any of the three fluids; feed fluid, membrane fluid, or sweep fluid.

The porous wall 5 on the interface of feed fluid and membrane liquid is designated as the "feed-side membrane." The feed-side membrane can be polymeric, metallic or ceramic materials, or a composite of any two. It can be hydrophobic or hydrophilic. The nominal pore size of the membrane can be up to 10 microns. The porous wall 6 on the interface of the membrane liquid and sweep/strip fluid is called the "enantiomer-side membrane." This membrane can be hydrophobic or hydrophilic with a nominal pore size up to 10 microns. Several types of commercially available membranes may be used including:

1) Porous polypropylene membranes with less than 0.5 micron pore size, such as:

Celgard membrane from Hoescht Celanese Corporation, Charlotte, N.C.,

Metrical PP membrane from Gelman Sciences, Ann Arbor, Mich.,

Microporous sheet from Tokuyama Corporation, 4–5 Nishi-Shinbashi, 1-Chome, Minato-Ku, Tokyo 105, Japan;

2) Porous PTFE Membranes:

Goretex PTFE membrane from W. L. Gore and Associates Inc., Elkton, Md.,

Fluoropore membranes from Millipore Corporation, Beford, Mass.

3) Other membranes:

Porous PVDF membranes,

Porous polyester membranes,

Porous polyethylene membranes, and

Porous nylon membranes;

4) Membranes obtained from modification of those above.

Also, in each of the three channels there may be one or more screen spacers/supports 13, 14. The screen has dual purposes; it offers mechanical support for the feed-side and sweep side membranes and creates turbulence as the fluids flow through them. The preferred screen materials are polymers, such as polypropylene, polyethylene, nylon and epoxy-coated nylon. The screen can be nonwoven and woven. It can also be a porous tubular membrane whose pores are filled with the liquid membrane. Usable screen materials include:

1) Naltex nettings with greater than 7 strands per inch from Nalle Plastics, Inc., Austin, Tex.;

2) Tricot or GUILTEC R0 channel fabric;

3) Polypropylene square net offered by Conwed Plastics, Minneapolis, Minn.; and

4) Polypropylene monofilament screen fabrics with greater than 20 mesh counts per inch offered by TETKO, Inc., Briarcliff Manor, N.Y.

The selectivity of the system is determined by the membrane liquid 7a, 7b which may or may not contain a carrier. The carrier can selectively and reversibly react or complex with the enantiomer. When a carrier is incorporated in the membrane liquid, the selective transport process is called carrier-mediated transport. When there is no carrier, the selective permeation of the enantiomer is accomplished by favorable partition/solution of the enantiomer into the membrane liquid.

Figure 2:
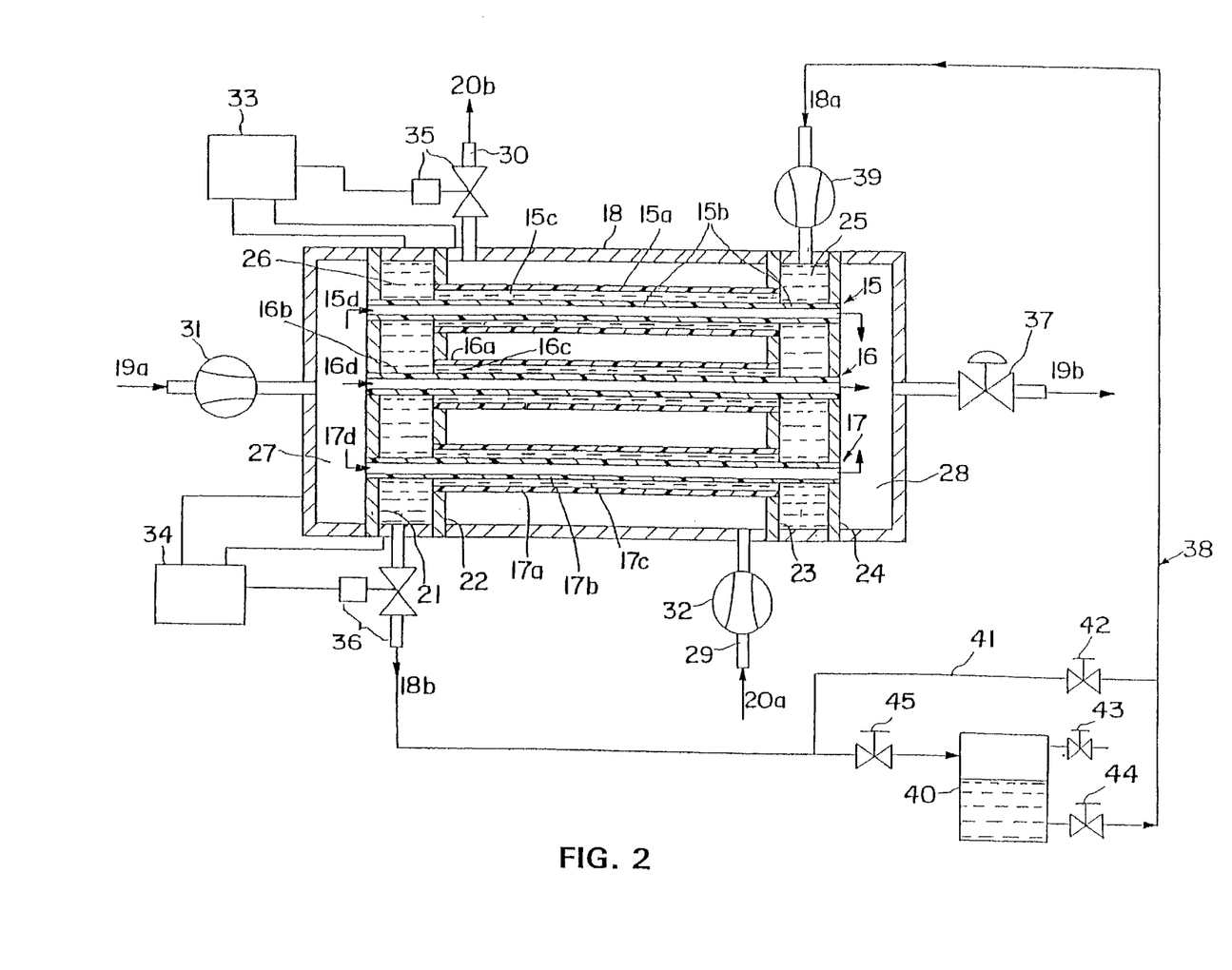
FIG. 2: is a cut-away view of tubular or hollow fiber liquid membrane system.
Figure 3:
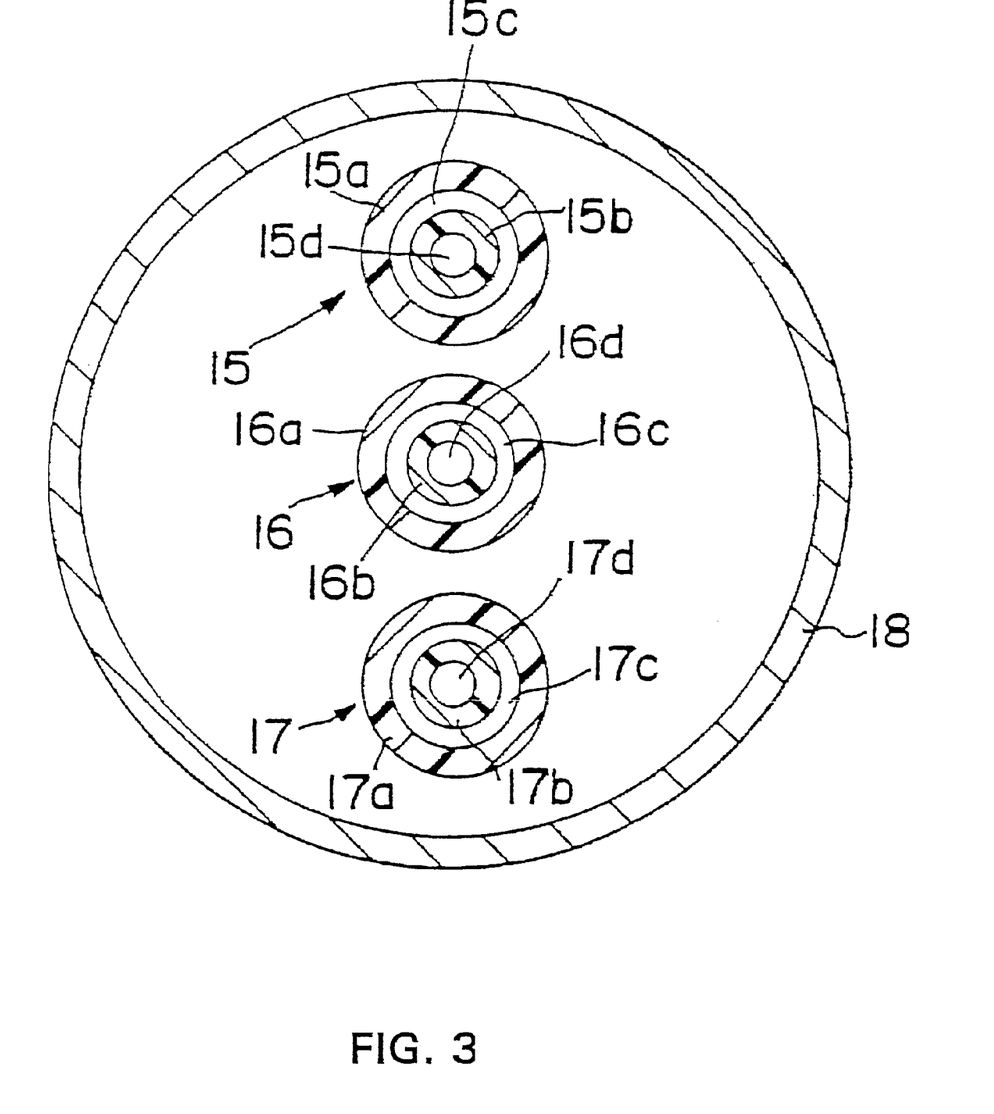
FIG. 3: is a cross section view of the tubular or hollow fiber liquid membrane module depicted in FIG. 2.

FIGS. 2 and 3 depict a Tubular or Hollow Fiber Membrane Module. Referring to FIG. 2, the liquid membrane module is formed by combining one or more membrane elements 15, 16, 17 in a module housing 18. Each membrane element includes two tubular or hollow fiber membranes, 15a, 15b, 16a, 16b, 17a, 17b with different diameters. As shown also in FIG. 3, the tube or hollow fiber with the smaller diameter, e.g. 15b, is located within the larger one 15a forming an annular gap 15c between the tubes.

Referring still to FIG. 2, the liquid membrane is formed by passing a selective-permeation membrane liquid 18a, 18b through the annular gaps 15c, 16c, 17c between the two tubes or fibers in each element. The annular gap may or may not contain a screen/spacer which is absent in FIGS. 2 and 3. The feed fluid 19a, 19b flows through the lumen side 15d, 16d, 17d of the inner tube of each element, while the sweep fluid 20a, 20b flows on the outside surface of the outer tube 15a, 16a, 17a, or vice versa.

There are four tube sheets in a module 21, 22, 23, 24, two on each end. The membrane liquid 18a, 18b enters the module from one end between the two tube sheets 23, 24; at the membrane liquid inlet manifold 25 the fluid distributes into the annular gaps of the membrane elements 15c, 16c, 17c and then exits at the other end between the two tube sheets 21, 22, at the membrane liquid outlet manifold 26.

The feed fluid 19a, 19b enters the module from one end of the module at the feed inlet manifold 27, distributes into the lumen side 15d, 16d, 17d of each inner tube (or fiber) in the module, and then exits the tubes into the feed outlet manifold 28 on the other end of the module. The sweep fluid flow 20a, 20b enters the module through a port 29 in the housing shall 18, flows along the outer surfaces of the outer tube/porous membrane 15a, 16a, 17a of each element, and exits the module through another port 30 on the shell. The entry and exit ports are apart from each other and close to the ends of the module.

A pump or compressor 31, 32 may be needed in both the enantiomer-depletion channel and enantiomer-enrichment channel to transport fluids in and through the module.

The module also includes pressure controllers 33, 34 and regulators 35, 36, 37 between the sweep fluid and membrane liquid channels and membrane liquid and enantiomer-depletion channels. There is a membrane circulation system 38 which includes a liquid pump 39, membrane liquid reservoir 40, circulation bypass 41 and pressure regulators, 42, 43, 44, 45.

The module may be manufactured in the following way:

(1) A bundle of concentric fibers are cut to length using a method that does not crimp the fiber ends together to ensure free movement of the inner fiber with respect to the outer fiber. For thermoplastics, heat and water jet cutting methods may be employed. The usual blade cutting methods are also appropriate.

(2) The fiber pairs are axially separated to a predetermined distance, exposing the inner fibers on one end of the bundle. Deionized air and removable liquid lubricating aids may be needed to remove static charges. Such aids also tend to strengthen the fibers against damage from handling. At this point, the fiber bundle is inserted into a suitable housing for the module.

(3) The now-empty outer fibers opposite the exposed inner fibers are heat sealed or predipped in potting compound to seal the ends to prevent the potting compound from plugging the fiber lumens.

(4) The exposed and sealed outer fibers are potted using standard potting materials, e.g., two component liquid urethane and/or epoxy resins and conventional centrifugal or dipping techniques. Afterward, the excess potting compound is cut away, using traditional cutting techniques. The sealed fiber ends are removed in the cut, allowing the inner fibers to slide past the cut surface of the outer fibers.

(5) Steps 2, 3, and 4 are repeated for the other end of the outer fibers. After the repeat of Step 2, and before the preliminary sealing of the outer fiber ends in Step 3, the outer fibers are cut to a new, reduced length suitable for allowing for a membrane solution entry and exit region in the final module. This repetition completes the potting of the outer fibers. The inner fibers at this time must still be axially free to move within the now potted outer fibers.

(6) The inner fibers are now sealed, potted, and cut using conventional techniques. Because fiber movement with respect to each other is no longer required after the inner fibers are centered, these steps will not be a technical challenge.

During the module assembly, the inner and outer fibers must be able to slide axially with respect to each other. During the fiber potting steps, the fibers also need to be taut and straight.

In operation, the module preferably contains a plurality of tubular or hollow fiber elements, but may contain only one element. The sweep fluid, feed fluid and membrane liquid are forced through their respective channels in a continuous and simultaneous fashion. Since the fluid channels are independent of each other, a liquid membrane is established within each element of the module.

As the feed fluid passes through the inner tube, one enantiomer is preferentially transported from the feed fluid, through the membrane liquid (which may or may not contain a carrier), and into the sweep fluid. The passage of the enantiomer to the sweep fluid is driven by the enantiomer's differential chemical potential across the liquid membrane. The membrane liquid preferably is continuously cycled through the membrane liquid channel as long as there is no degradation in the carrier concentration if a carrier is used. However, the membrane liquid could be stationary. A membrane liquid reservoir is provided between the membrane liquid inlet and outlet ports for storing the circulation membrane liquid. A bleed of membrane liquid may be drawn and replaced with fresh membrane liquid.

The feed and sweep fluids may be passed through the elements in a "once through" mode, or a fixed quantity may be continuously cycled through the elements to remove the enantiomer from a fixed amount of feed fluid. In the "once-through" mode, steady streams of sweep and feed fluids are passed through the module and not recycled. In either mode, the enantiomer-enriched sweep fluid is removed through the port 30 on the housing of the shell.

In the alternative, if the enantiomers are gaseous, the module may be operated by closing the sweep fluid inlet port and using no sweep fluid. In this mode, the sweep fluid outlet port may be connected to a standard vacuum pump and/or a condenser to draw the enantiomer out of the module from the enantiomer enrichment channels.

The above-described liquid membrane module is disclosed in U.S. Pat. No. 5,580,452 which is incorporated herein by reference.

Figure 4A:
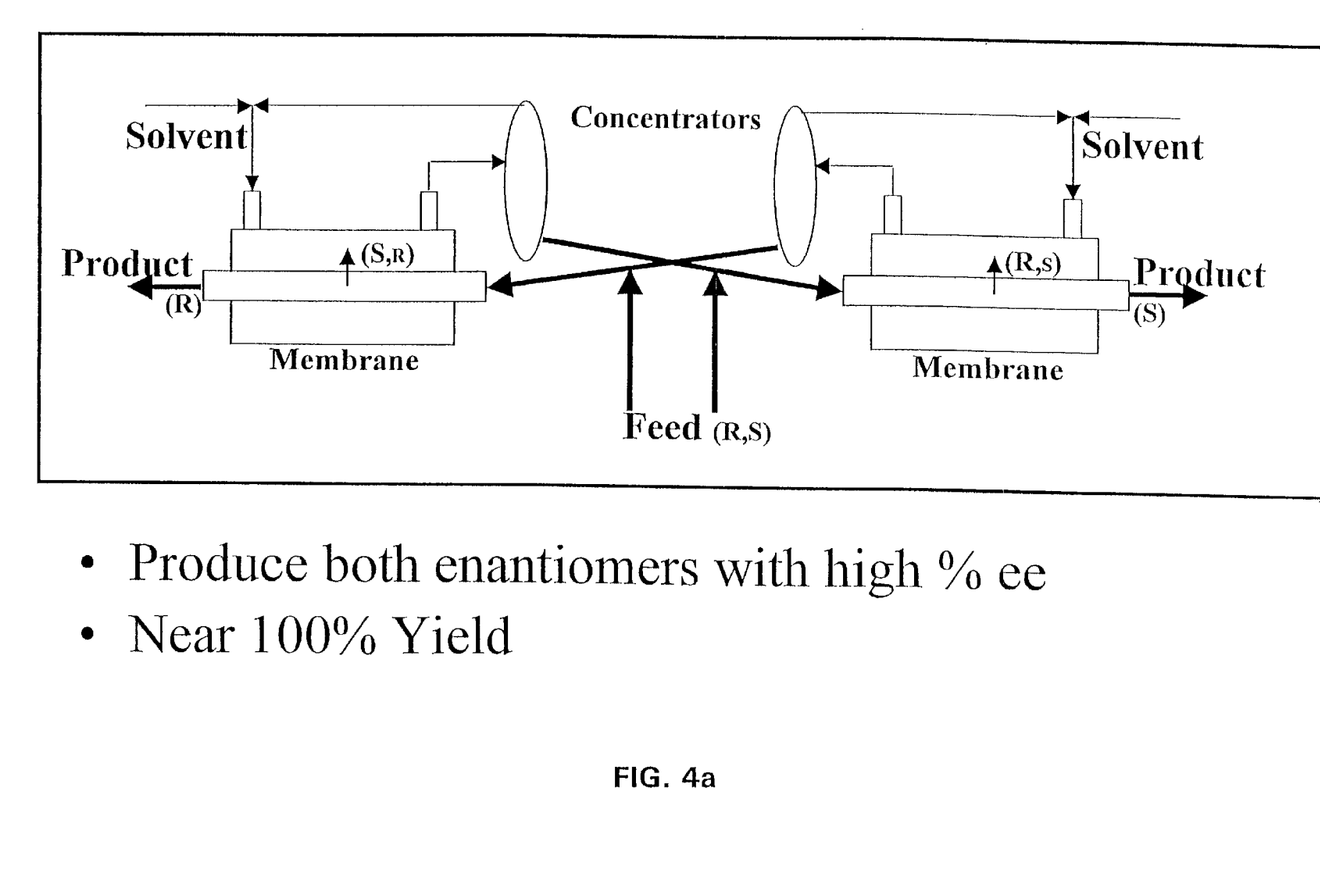
FIGS. 4a & 4B: are schematics of representative assemblies of the invention.

The module shown in FIG. 1a would be used for separating one enantiomer from a racemic mixture. However, the method of this invention can be used for isolating both enantiomers simultaneously. FIG. 4a shows an assembly of two liquid membrane modules as well as other components to enable the isolation of two enantiomers in high percent (%) ee (enantiomeric excess) which may be calculated as follows:

$$\% \text{ ee of } R = \frac{[R] - [S] \times 100}{[R] + [S]}$$

where [R] and [S] are the concentrations of the R enantiomer and of the S enantiomer respectively. To calculate the % ee of the S enantiomer [R] and [S] are reversed in the above formula.

Figure 4B:
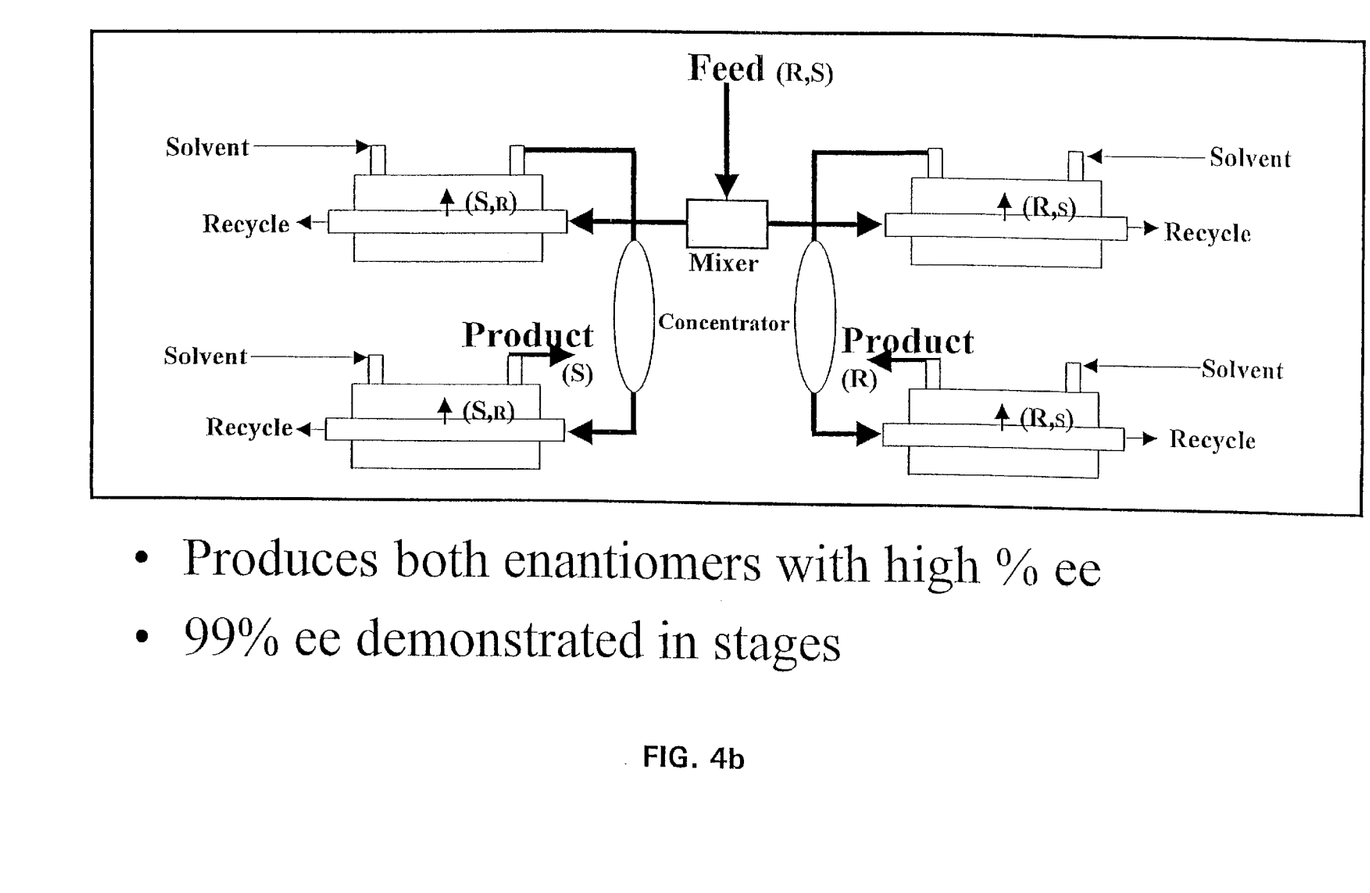

A commercial enantiomer separating unit, will likely be an assembly of two or more liquid membrane (L.M.) modules arranged as shown in FIG. 4b. In one design there are two sets of two L.M. modules, one set isolating one enantiomer (for Example S) and the other separating a different enantiomer (for Example R). As may be seen from said figure, the racemic mixture is fed into the first L.M. module of each set where the sweep is enriched with a different enantiomer. Eventually the sweep preferably goes through a concentration which removes the solvent and concentrates the enantiomer which is then passed through the second L.M. module where the sweep contains essentially pure enantiomer. In each of the designs represented in FIG. 4a and FIG. 4b, an epimerizer may be preferably also employed immediately following the concentrator. The use of an epimerizer is known to those skilled in the art. Essentially, it is a reactor in which a non-racemic mixture of enantiomers is reacted with another material, such as for example, an acid or a base or other compounds known in the art, to reestablish a racemic mixture. Without the use of an epimerizer, there would be a limit to the ability to separate one enantiomer from the other because as the concentration of one enantiomer increases in a sweep, the L.M. would no longer be able to separate the two enantiomers in such disparate concentrations. In the above-described assemblies, additional accessories or components may be advantageously used, such as pumps for circulating various fluids, a temperature control.

During the separation process, it is common for the pressure in the various fluids to fluctuate which may cause the liquid in the liquid membrane to be forced out of the pores if a prior art flat sheet liquid membrane is used. This would result in the mixing of the feed and sweep fluids. The pressure may fluctuate up to 40 or 50 psi which may force the liquid membrane out of the pores in liquid membranes. In the prior art liquid membranes, such as the flat sheet L.M., it is not possible to replenish the liquid in the pores. In the L.M. employed in the present invention, the liquid would be quickly replenished and the process would continue without any damage to the module and without interruption in the separation.

EXAMPLE 1

Separation of R Enantiomer from Racemic N-(3,5-dinitrobenzoyl leucine

The module as shown in FIG. 1a was used in this separation. The liquid membrane consisted of 40 mM of (R)-N-(1-naphthyl) leucine octadecyl ester (the carrier) and tetrahexyl ammonium chloride (PTA) in dodecane; the sweep was an aqueous solution of 50 mM of potassium phosphate ($KH_2PO_4$) a buffer that had pH 7. The feed was 10 mM of racemic N-(3-5-dinitrobenzoyl) leucine in water.

The module had the following dimensions: 14 fiber-in-fiber pairs, the outer fiber had an outer diameter of 0.774 mm and an inner diameter of 0.631 mm, whereas the inner fiber had an outer diameter of 1.07 mm and an inner diameter of 0.876 mm. The annular space was 51 $\mu$m thick. Inner fiber length was approximately 8 inches and the outer fiber length approximately 10 inches. The surface area was calculated to be 69 $cm^2$ based on the outer surface of the inner fiber. The volume of the feed and sweep solutions was 25 mL each and the liquid membrane reservoir volume was 5 mL, including the volume outside the membrane module.

Figure 1B:
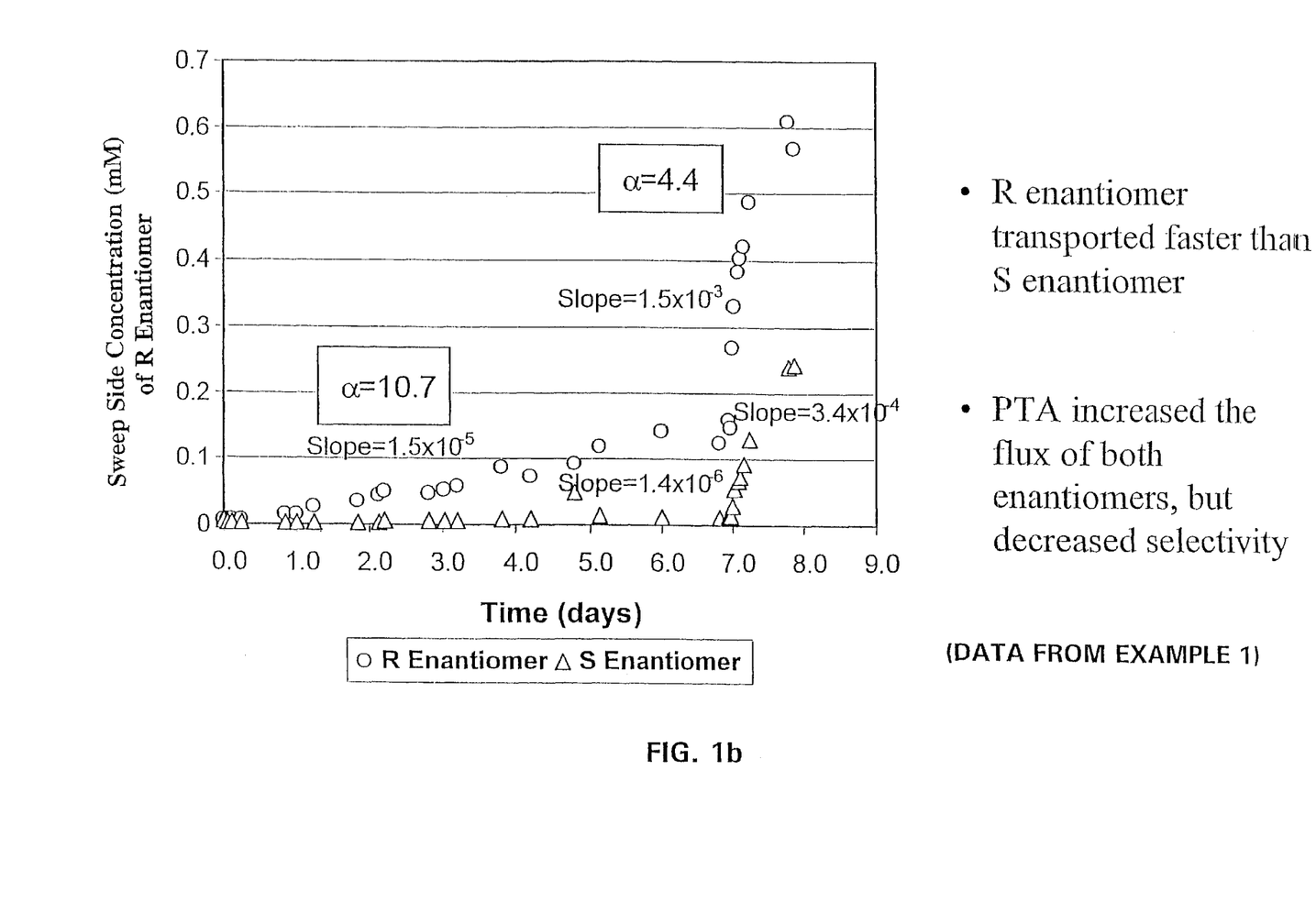
FIG. 1b: contains data from Example 1.

Initially 5 mM of the PTA was used in the sweep and the racemic mixture was recirculated through the module for six (6) days. The R enantiomer transported about 10.4 times faster than the S enantiomer as shown in FIG. 1b.

On day 7 of the PTA, concentration was increased to 50 mM. Immediately thereafter, the flux (slope) of the R Enantiomer increased by a factor of 100, which means that the transport of this enantiomer increased 100 times, and the flux (slope) of the S Enantiomer increased by a factor of 243, or the transport of this enantiomer increased 243 times. The ratio of the slopes ($\alpha$), which is the measure of selectivity, dropped from 10.7 to 4.4. The results of this example are shown in FIG. 1b.

Applicant does not intend to be limited to the specific embodiments disclosed above. One skilled in the art will understand that many variations and alterations are possible within the scope of the invention. It is, therefore, intended to encompass all such variations and modifications.

What is claimed is:

1. A method of separating enantiomers in a supported liquid membrane module containing at least one tubular liquid membrane element which includes a first tubular membrane located within a second tubular membrane with an annular gap defined between the first tubular membrane and the second tubular membrane such that the liquid membrane is contained in said annular gap and said tubular membranes contain pores; said supported liquid membrane module comprises a liquid membrane, a feed fluid containing a racemic mixture and a sweep fluid which contains the separated enantiomer, such that said feed fluid and said sweep fluid are adjacent to, but on opposite sides of, said liquid membrane and the feed fluid and the sweep fluid have a substantially continuous interfacial contact along the length of the liquid membrane, said method comprising:

a) contacting liquid membrane with said feed fluid;
   b) transporting preferentially one enantiomer from the feed fluid into the liquid membrane;
   c) contacting liquid membrane with said sweep fluid;
   d) transporting said preferential enantiomer from the liquid membrane into the sweep fluid; and
   e) recovering the transported preferential enantiomer from the sweep fluid.

2. A method of claim 1, wherein the liquid membrane is substantially stationery.

3. A method of claim 1, wherein the liquid membrane is a moving liquid membrane.

4. A method of claim 3, wherein the separated enantiomer is gassous.

5. A method of claim 3, wherein said feed fluid and sweep fluid contain a solvent.

6. A method of claim 5, wherein said liquid membrane additionally contains a carrier.

7. A method of claim 6, wherein said liquid membrane additionally contains a phase transfer agent.

8. A method of claim 7, wherein the feed fluid and the sweep fluid each contain a solvent and the solvent in both the feed fluid and the sweep fluid is the same, but said solvent is different than said liquid membrane which is immiscible with the solvent in both the feed and the sweep fluids.

9. A method of claim 8, wherein the sweep fluid contains additionally an enantiomer solubility enhancer.

10. A method of claim 9, wherein the pH of the sweep fluid is adjusted to maximize the solubility of the preferential enantiomer.

11. A method of claim 8, wherein the enantiomers have poor partitioning into the liquid membrane, said method wherein the pores of the tubular membrane are filled with the feed and/or the sweep liquids.

12. A method of claim 8, wherein enantiomers have good partitioning into the liquid membrane, said method wherein the pores of the tubular membrane are filled with the liquid membrane.

13. A method of claim 8, wherein the solvent in the sweep has preferential solubility for one enantiomer.

14. A method of claim 7, wherein the solvents in the feed fluid and in the sweep fluid are different and both said solvents are different from and immiscible with the liquid membrane.

15. A method of claim 14, wherein the solvent in the sweep has preferential solubility for one enantiomer.

16. A method of separating enantiomers in a liquid membrane module, said method comprising passing a fluid containing said enantiomers through a module containing:
   a) a housing which encloses the liquid membrane module;
   b) at least one supported membrane element that includes two tubular or hollow fiber membranes of different diameters such that said tube or hollow fiber with the smaller diameter is located within the tubular or hollow fiber with the larger diameter;
   c) a membrane liquid inlet at one end of the module through which the membrane liquid enters the module and fills the gap between the hollow fiber with the smaller diameter and the hollow fiber of the larger diameter and a membrane liquid outlet through which said membrane liquid exits the module;
   d) a feed fluid inlet at one end of the module through which the feed fluid containing enantiomers enters the module so that the feed fluid circulates through the hollow fiber with the smaller diameter, and a feed fluid outlet through which said feed fluid exits the module;
   e) an entry port in said housing through which a sweep fluid which is a solvent for preferential enantiomers passing through the hollow fiber with the larger diameter and enters the module and flows along the outer surfaces of the liquid membrane receiving an enantiomer and exits through the exit port in said housing; and
   f) isolating the enantiomer from the sweep fluid; wherein the feed fluid and the sweep fluid are adjacent to, but on opposite sides of the liquid membrane and the feed and sweep fluids have a substantially continuous interfacial contact along the length of the liquid membrane.

17. A method of claim 16, wherein said liquid membrane additionally contains a carrier.

18. A method of claim 17, wherein said liquid membrane additionally contains a phase transfer agent.

19. A method of claim 17, wherein the feed fluid additionally contains a solvent which is the same as the sweep fluid, but is different than the liquid membrane and is immiscible with the solvent in both the feed and the sweep fluids.

20. A method of claim 19, wherein the sweep fluid contains additionally an enantiomer solubility enhancer.

21. A method of claim 20, wherein the pH of the sweep fluid is adjusted to maximize the solubility of one enantiomer.

22. A method of claim 19, wherein the enantiomers have poor partitioning into the liquid membrane, said method wherein the pores of the walls of the liquid membrane are filled with the feed and/or the sweep liquids.

23. A method of claim 19, wherein enantiomers have good partitioning into the liquid membrane, said method wherein the pores of the walls of the liquid membrane are filled with the liquid membrane.

24. A method of claim 17, wherein the solvents in the feed fluid and in the sweep fluid are different and both said solvents are different from and immiscible with the liquid membrane.

25. A method of claim 16, wherein the sweep fluid is recirculated through said liquid membrane module.

26. A method of claim 25, wherein said sweep fluid is epimerized prior to recirculating through the liquid membrane.

27. A method of separating enantiomers in a supported liquid membrane module containing at least one tubular liquid membrane element which includes a first tubular membrane located within a second tubular membrane with an annular gap defined between the first tubular membrane and the second tubular membrane such that the liquid membrane is contained in said annular gap and said tubular membranes contain pores; said supported liquid membrane module comprises a liquid membrane, a feed fluid containing enantiomers and a sweep fluid which contains the separated enantiomer, such that said feed fluid and said sweep fluid are adjacent to, but on opposite sides of, said liquid membrane and the feed fluid and the sweep fluid have a substantially continuous interfacial contact along the length of the liquid membrane, said method comprising:
   a) contacting liquid membrane with said feed fluid;
   b) transporting preferentially one enantiomer from the feed fluid into the liquid membrane;
   c) contacting liquid membrane with said sweep fluid;
   d) transporting said preferential enantiomer from the liquid membrane into the sweep fluid; and
   e) recovering the transported preferential enantiomer from the sweep fluid.

28. A method of claim 27, wherein the liquid membranes are moving liquid membranes.

29. A method of claim 28, wherein at least one concentrator is employed.

30. A method of claim 29 wherein at least one epimerizer is employed.

31. A method of claim 30, wherein the sweep fluid is recirculated through said liquid membrane modules.

32. A method of claim 27 wherein said module contains at least four moving liquid membranes, at least two concentrators and at least two epimerizers.

* * * * *